(12) United States Patent
Hoffman et al.

(10) Patent No.: US 8,828,072 B2
(45) Date of Patent: Sep. 9, 2014

(54) EXTENDABLE FLUSHING SYSTEM

(75) Inventors: Grant T. Hoffman, Bloomington, IN (US); Chase Wooley, Floyds Knobs, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 380 days.

(21) Appl. No.: 13/186,208

(22) Filed: Jul. 19, 2011

(65) Prior Publication Data

US 2012/0022632 A1    Jan. 26, 2012

Related U.S. Application Data

(60) Provisional application No. 61/366,034, filed on Jul. 20, 2010.

(51) Int. Cl.
    A61F 2/06        (2013.01)
    A61F 2/966       (2013.01)
    A61F 2/95        (2013.01)
    A61M 25/01       (2006.01)
    A61M 25/06       (2006.01)

(52) U.S. Cl.
    CPC ......... *A61F 2/966* (2013.01); *A61F 2002/9517* (2013.01); *A61M 2025/0175* (2013.01); *A61M 25/01* (2013.01); *A61M 2025/0681* (2013.01); *A61F 2002/9665* (2013.01)
    USPC ........... 623/1.11; 600/156; 600/158; 600/159

(58) Field of Classification Search
    CPC ................ A61F 2002/9517; A61F 2002/9665; A61F 2/966; A61F 2/95; A61F 2/962; A61M 2025/0175; A61M 2025/0681; A61M 25/01
    USPC .................................. 623/1.11; 600/159, 158
    See application file for complete search history.

(56) References Cited

U.S. PATENT DOCUMENTS

| | | | | |
|---|---|---|---|---|
| 5,364,198 | A  * | 11/1994 | Skenderi ....................... | 401/138 |
| 5,391,172 | A    | 2/1995  | Williams et al. | |
| 6,786,865 | B2 * | 9/2004  | Dhindsa ........................ | 600/159 |
| 2009/0024133 | A1 | 1/2009 | Keady et al. | |

* cited by examiner

*Primary Examiner* — Gregory Anderson
(74) *Attorney, Agent, or Firm* — Buchanan Nipper

(57) ABSTRACT

An extendable flushing system, a delivery system including an extendable flushing system and a method of flushing a delivery system are provided. The extendable flushing system includes flexible tubing having an extended configuration and a compressed configuration, a first tubing end and a second tubing end. The extendable flushing system also includes a flush port and a shuttle assembly. The flush port includes a first lumen operably connected to the first tubing end and an opening configured to receive fluid therethrough. The shuttle assembly is operably connected to the second tubing end forming a fluid flow path with the flush port and the shuttle assembly. The shuttle assembly is configured to be fluidly connected to a lumen of an elongate device. The shuttle assembly is movably positionable relative to the flush port and configured to move the flexible tubing between the compressed configuration and the extended configuration.

17 Claims, 10 Drawing Sheets

EXTENDABLE FLUSHING SYSTEM

RELATED APPLICATIONS

This application claims the benefit of the filing date under 35 U.S.C. §119(e) of Provisional U.S. patent application Ser. No. 61/366,034, filed Jul. 20, 2010, which is incorporated by reference in its entirety.

BACKGROUND

Stent delivery systems for expandable stents typically employ a push-pull mechanism to introduce the stent into the body. For example, stent delivery systems generally include an outer sheath coaxially disposed and slidable over an inner catheter. The stent is disposed at the distal end of the delivery system in between the inner catheter and the outer sheath. The inner catheter and the outer sheath move coaxially with respect to each other to expose the stent at a delivery position. A self-expanding stent may be deployed at the delivery site by proximally pulling back the outer sheath relative to the inner catheter until the stent is exposed and expands away from the inner catheter. An outer sheath may also be used with balloon expandable or other types of expandable stents, for example to protect the stent during delivery to the patient. Some of the stent delivery systems also include a flushing port.

There are numerous drawbacks to the above push-pull delivery device. For example, utilizing a conventional push-pull delivery device may cause the physician to inadvertently use excessive force and pull back the outer sheath too far, thereby prematurely deploying the stent in an incorrect position within a body lumen. At this step in the procedure, repositioning of the stent becomes difficult, if not impossible, because the stent has already radially self-expanded into the body lumen. Additionally, controlled retraction of the outer sheath may not be achieved when the physician is manually retracting the outer catheter. Manual retraction of the outer sheath may lead to inadvertent jerking back of the outer sheath and difficulty in proper placement of the stent. Furthermore, two hands are typically needed to deploy the prosthesis with a push-pull mechanism. One hand may be required to hold the inner catheter while the other hand pulls the outer sheath and slides it back over the inner catheter. The use of two hands prevents the physician from performing another task during the procedure.

In view of the drawbacks of the typical push-pull delivery system, a delivery system that can increase the control, accuracy and ease of placement during deployment of a stent has been developed as described in U.S. Patent Publication 2009/0024133. In some situations, it is advantageous to include a flushing system with a stent delivery system to flush air or other particles from the delivery system prior to use. What is needed is a flushing system that can be used with a controlled stent delivery system that allows the physician to flush the stent within a flushable stent chamber without interfering with the delivery system control for moving the outer sheath relative to the inner catheter. Although the flushing system described below may be useful with the delivery system for increasing the control, accuracy and ease of placement during deployment of the stent, the flushing system may also solve other problems.

BRIEF SUMMARY

Accordingly, it is an object of the present invention to provide a system and a method having features that resolve or improve on one or more of the above-described drawbacks.

In one aspect of the present invention, an extendable flushing system is provided for use with a medical device such as a stent delivery system. The extendable flushing system includes flexible tubing having an extended configuration and a compressed configuration, a first tubing end and a second tubing end. The extendable flushing system also includes a flush port and a shuttle assembly. The flush port includes a first lumen operably connected to the first tubing end and to an opening configured to receive fluid therethrough. The shuttle assembly is operably connected to the second tubing end forming a fluid flow path with the flush port and the shuttle assembly. The shuttle assembly is configured to be fluidly connected to a lumen of an elongate shaft. The shuttle assembly is movably positionable relative to the flush port and configured to move the flexible tubing between the compressed configuration and the extended configuration.

In another aspect of the present invention, a delivery system is provided. The delivery system includes a handle and an outer sheath having a lumen, the outer sheath at least partially positioned within the handle. The delivery system also includes an inner catheter coaxially positioned within at least a portion of the outer sheath. The outer sheath is longitudinally movable relative to the inner sheath. The delivery system further includes an extendable flushing system positioned at least partially within the handle. The extendable flushing system includes flexible tubing having an extended configuration and a compressed configuration, a first tubing end and a second tubing end. The extendable flushing system also includes a flush port and a shuttle assembly. The flush port includes a first lumen operably connected to the first tubing end and to an opening configured to receive fluid therethrough. The shuttle assembly is operably connected to the second tubing end forming a fluid flow path with the flush port and the shuttle assembly. The shuttle assembly is configured to be fluidly connected to the lumen of the outer sheath. The shuttle assembly is movably positionable relative to the flush port and configured to move the flexible tubing between the compressed configuration and the extended configuration.

In another aspect of the present invention, a method of flushing a delivery system having an outer sheath movable relative to an inner catheter is provided. The method includes providing an extendable flushing system. The extendable flushing system includes flexible tubing having an extended configuration and a compressed configuration, a first tubing end and a second tubing end. The extendable flushing system also includes a flush port and a shuttle assembly. The flush port includes a first lumen operably connected to the first tubing end and to an opening configured to receive fluid therethrough. The shuttle assembly is operably connected to the second tubing end forming a fluid flow path with the flush port and the shuttle assembly. The shuttle assembly is movably positionable relative to the flush port and configured to move the flexible tubing between the compressed configuration and the extended configuration. The method also includes connecting a fluid source to the opening in the flush port and injecting fluid into the port through the tubing to the shuttle assembly and into the lumen of the outer sheath.

DETAILED DESCRIPTION

Figure 1:
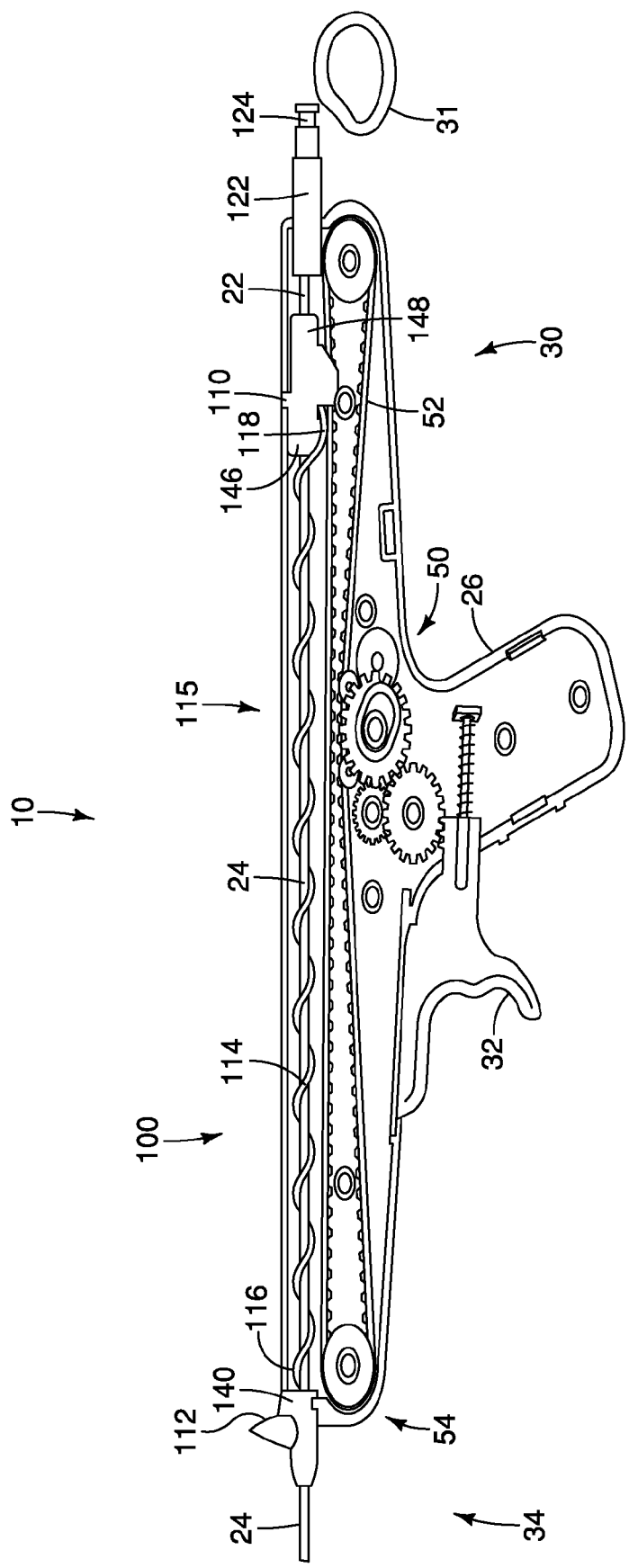
FIG. 1 is a partial side view of delivery system including an extendable flushing system in accordance with an embodiment of the present invention.

The invention is described with reference to the drawings in which like elements are referred to by like numerals. The relationship and functioning of the various elements of this invention are better understood by the following detailed description. However, the embodiments of this invention are not limited to the embodiments illustrated in the drawings. It should be understood that the drawings are not to scale, and in certain instances details have been omitted which are not necessary for an understanding of the present invention, such as conventional fabrication and assembly.

As used in the specification, the terms proximal and distal should be understood as being in the terms of a physician delivering the stent to a patient. Hence the term "distal" means the portion of the delivery system that is farthest from the physician and the term "proximal" means the portion of the delivery system that is nearest to the physician.

FIG. 1 illustrates a delivery system 10 including an extendable flushing system 100. Briefly, the delivery system 10 includes an inner catheter 22 and an outer sheath 24 that is coaxially movable relative to the inner catheter 22. The delivery system 10 includes a handle 26 at a proximal end 30 of the system 10 through which the inner catheter 22 and outer sheath 24 at least partially extend. The handle 26 further includes a trigger 32 that is operably connected to the outer sheath 24 to move the outer sheath 24 relative to the inner catheter 22 to expose a stent 28 (shown in FIG. 2) at a distal end 34 of the delivery system 10. The delivery system 10 further includes an internal gear-pulley mechanism 50 that allows bidirectional movement of the outer sheath 24. A movable belt 52 is connected to a shuttle assembly 110 that is operably connected to the outer sheath 24. Together the movable belt 52, the gear-pulley mechanism 50 and the shuttle assembly 110 cooperate to longitudinally move the outer sheath 24 to expose and re-cover the stent 28. The handle 26 is provided with a switch 56 that may be activated to change the direction of longitudinal movement of the outer sheath 24 relative to the inner catheter 22 by changing the direction of the movable belt 52 and operably shifting the gear-pulley mechanism 50. The delivery system, including the gear-pulley mechanism, the belt and the switch, is explained in greater detail in U.S. Patent Publication 2009/0024133, which is incorporated by reference in its entirety herein.

Figure 2:
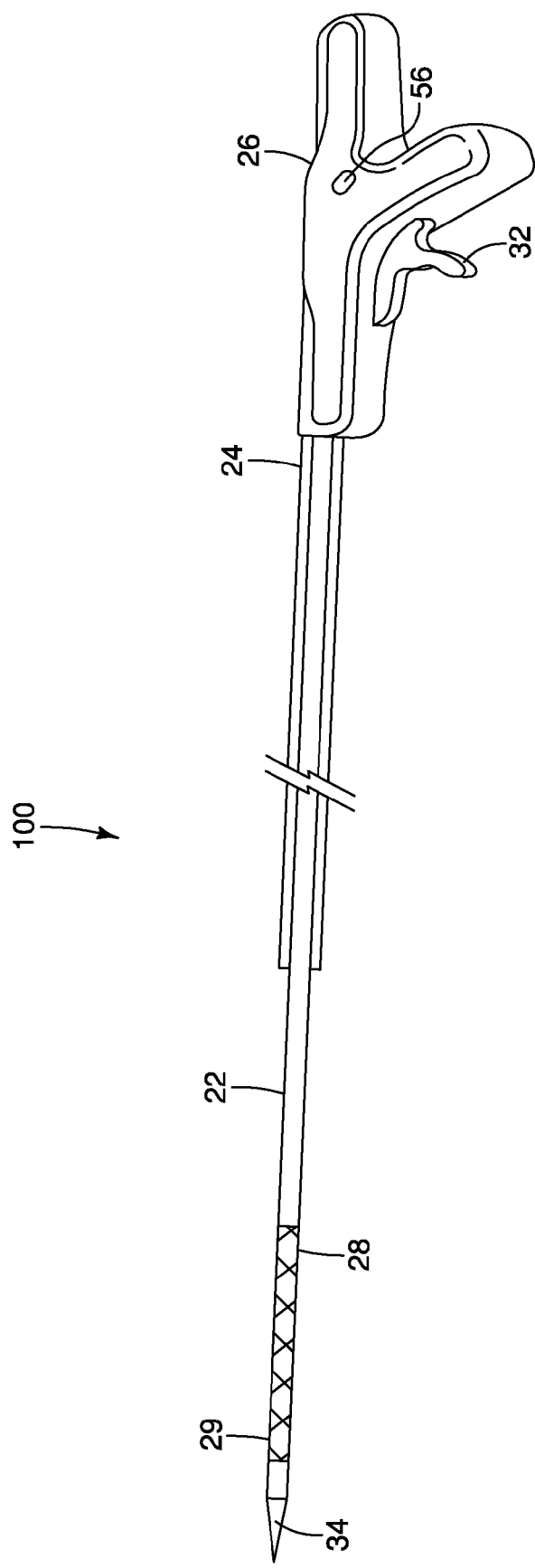
FIG. 2 is side view of the delivery system shown in FIG. 1.

The extendable flushing system 100 shown in FIG. 1 is operably connected to the delivery system 10 that longitudinally moves the outer sheath 24 relative to the inner catheter 22 in a controlled and accurate movement. The extendable flushing system 100 allows the physician to flush the delivery system 10 in all positions of the movable outer sheath 24. The extendable flushing system 100 includes the shuttle assembly 110, a distal flush port 112 and a flexible tubing 114. As shown in FIG. 1, the extendable flushing system 100 has an extended configuration 115 where the shuttle assembly 110 is moved away from the distal flush port 112 and towards the proximal end 30 of the handle 26. The flexible tubing 114 is extended between the distal flush port 112 and the shuttle assembly 110 for fluidly connecting the distal flush port 112 and the shuttle assembly 110 to establish a flow path to provide fluid within a lumen of the outer sheath 24 by connection of the outer sheath 24 to the shuttle assembly 110. As shown in FIG. 1, the distal flush port 112 may be mounted on a distal portion 54 of the handle 26 so that the distal flush port 112 is in a fixed position relative to the handle 26. The shuttle assembly 110 is longitudinally movable within the handle 26 along the inner catheter 22 to move the outer sheath 24 proximally and distally relative to the inner catheter 22. The tubing 114 is connected to the distal flush port 112 at a first end 116 of the tubing 114 and to the shuttle 110 at a second end 118 of the tubing 114. The tubing 114 is flexible so that the length of the tubing 114 elongates and compresses as the shuttle assembly 110 moves proximally and distally. With the shuttle assembly 110 positioned near the proximal end 30 of the handle 26, the outer sheath 24 is retracted away from the stent 28 as shown in FIG. 2.

Figure 3:
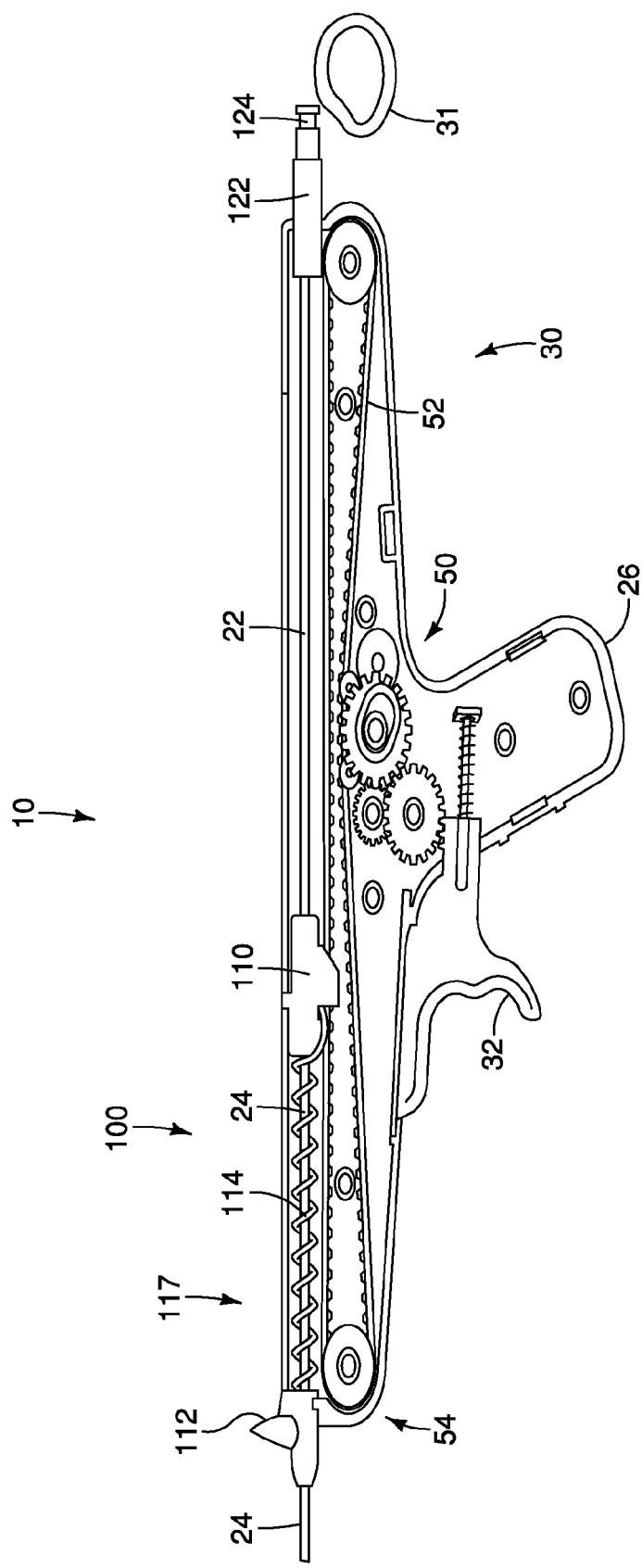
FIG. 3 is a partial side view of the delivery system shown in FIG. 1 illustrating the flushing system in a compressed configuration.

FIG. 3 illustrates the extendable flushing assembly 100 in a compressed configuration 117 where the shuttle assembly 110 is moved toward the distal flush port 112 and away from the proximal end 30 of the handle 26. The flexible tubing 114 is compressed along the outer sheath 24 and remains connected between the distal flush port 112 and the shuttle assembly 110 so that flushing between the outer sheath 24 and the inner catheter 22 is possible. With the shuttle assembly 110 advanced toward the distal flush port 110 as shown in FIG. 3, the outer sheath 24 covers the stent 28 at the distal end 34 of the delivery system 10. As shown in FIGS. 1 and 3, and by way of non-limiting example, the tubing 114 may be provided in a coil wound around a portion of the outer sheath 24 so that the coil expands when the shuttle assembly 110 is moved proximally and the coil compresses when the shuttle 110 is moved distally. The tubing 114 may be provided in any configuration that is suitable for conducting liquid therethrough in all positions of the shuttle assembly 110.

The flushing system 100 may also include an end assembly 122 at the proximal end 30 of the handle 26 for receiving the inner catheter 22 and a lock wire 29 operably connected to the stent 28 to releasably lock the stent 28 to the inner catheter 22 until the stent 28 is ready to be fully deployed. The lock wire 29 is shown in FIG. 2 and extends through a portion of the stent 28 and extends proximally to the proximal end 30 of the handle 26. The lock wire 29 may be connected to a loop 31 at the proximal end 30 of the handle 26 as shown in FIGS. 1 and 3 so that the lock wire 29 may be proximally withdrawn from the stent 28 by pulling the loop 31 proximally and thus releasing the stent 28 from the inner catheter 22. The end assembly 122 may be fixed in position at the proximal end 30 of the handle 26. An adapter 124, such as a luer adapter, may be included proximal to the end assembly 122 and adapted to connect to the inner catheter 22 at the proximal end 30 of the handle 26. In some embodiments, the inner catheter 22 and the adapter 124 may be fixed in position relative to the handle 26 and in other embodiments, the inner catheter 22 and the adapter 124 may be longitudinally movable relative to the handle 26 and to the outer sheath 24 so that both the inner catheter 22 and outer sheath 24 and movable relative to each other and to the handle 26 to control the release of the stent 28.

Figure 4A:
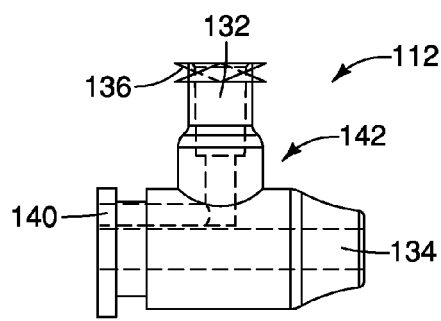
FIG. 4A is a side view of an embodiment of a distal port of the flushing system.
Figure 4B:
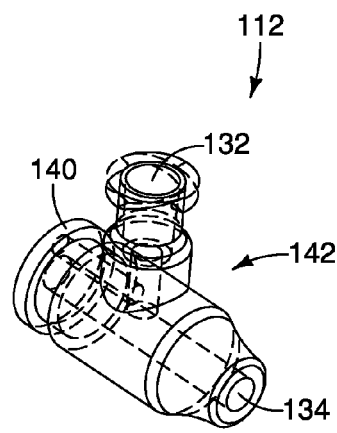
FIG. 4B is a perspective view of the distal port shown in FIG. 4A.

Enlarged views of an exemplary distal flush port 112 are shown in FIGS. 4A and 4B. As shown, the distal flush port 112 includes a first lumen 132 and a second lumen 134. The first lumen 132 is configured to receive a fluid therethrough and the second lumen 134 is configured to receive the outer sheath 24 therethrough. As shown, the distal flush port 112 may include an adapter 136, such as a luer adapter, at a first opening 138 of the first lumen 132 for connection to a syringe or tubing to deliver the fluid through the first lumen 132. The first opening 138 may be provided on a top side 142 of the distal flush port 112 to provide access to the flush port 112 during stent delivery. A second opening 140 of the first lumen 132 connects to the first end 116 of the tubing 114 to conduct the fluid through the tubing 114. (See FIG. 1.) The second lumen 134 is sized and shaped to allow the outer sheath 24 to be slidably received therethrough so that the outer sheath 24 is movable proximally and distally with respect to the distal flush port 112. In some embodiments, the distal flush port 112 may be movable relative to the handle 26. The movable distal flush port 112 may be operably connected to the belt 52 and may include grooves to mate with protrusions of the belt similar to the shuttle assembly 110 as described below.

Figure 5A:
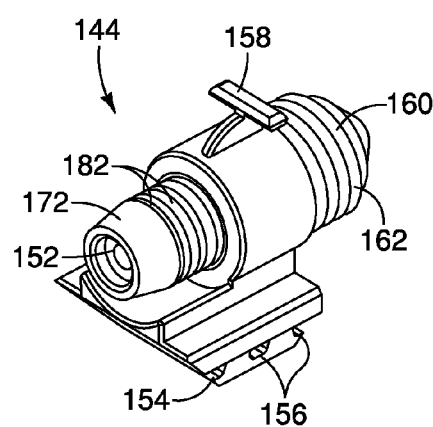
FIG. 5A is a perspective view of an embodiment of a shuttle body of the flushing system.
Figure 5B:
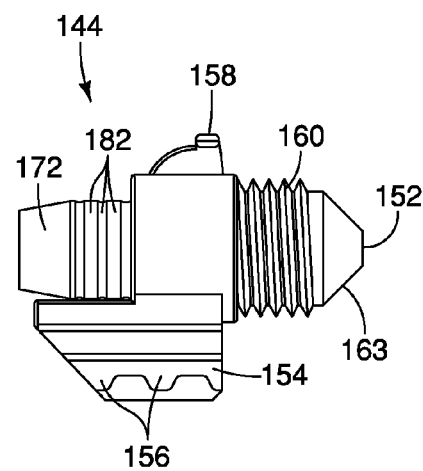
FIG. 5B is a side view of the shuttle body shown in FIG. 5A.
Figure 5C:
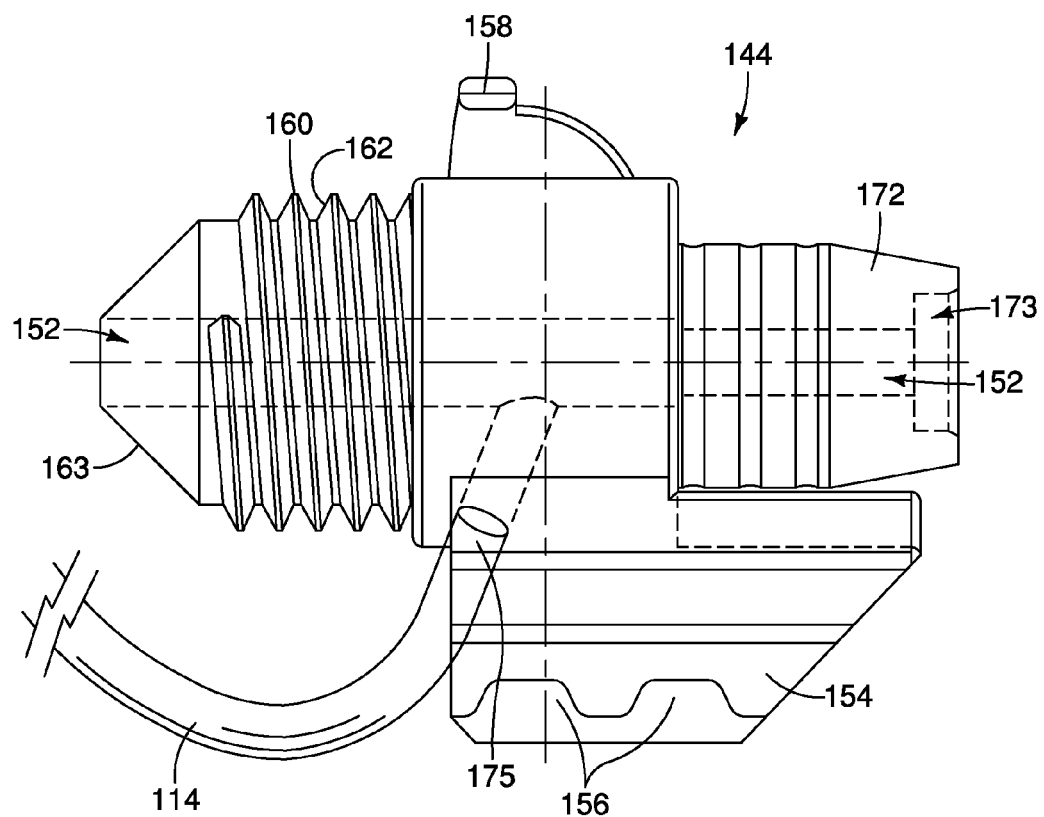
FIG. 5C is a side view of the shuttle body shown in FIG. 5A.
Figure 6:
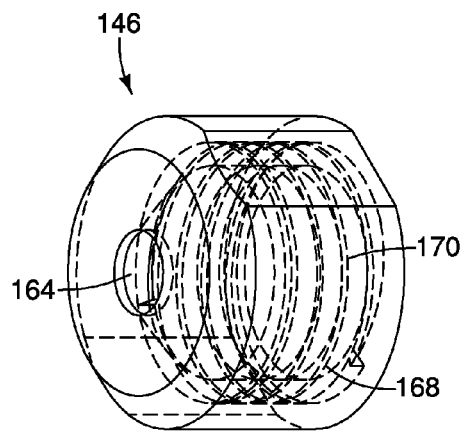
FIG. 6 is a perspective view of an embodiment of a cap of the flushing system.
Figure 7:
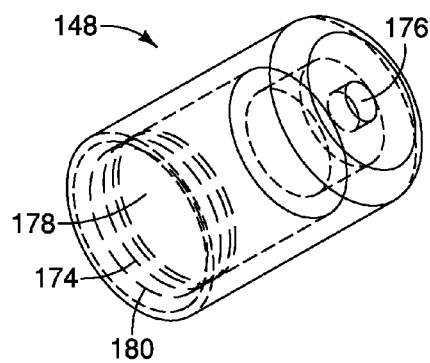
FIG. 7 is a perspective view of an embodiment of a check flow valve of the flushing system.

Enlarged views of portions of the shuttle assembly 110 are shown in FIGS. 5A-7. A shuttle body 144 of the shuttle assembly 110 is shown in FIGS. 5A-5C. The shuttle assembly 110 may also include a cap 146 (FIG. 6) and a check flow valve 148 (FIG. 7). The shuttle body 144 includes a lumen 152 extending therethrough that is sized and shaped for reception of the inner catheter 22. The shuttle body 144 is slidably movable over the inner catheter 22 to move the outer sheath 24 relative to the inner catheter 22. The shuttle body 144 further includes an opening 154 having grooves 156 therein that correspond to protrusions on the belt 52 (shown in FIGS. 1 and 3) that mate together with the grooves 156 to move the shuttle assembly 110 and the outer sheath 24 proximally and distally to uncover and resheath the stent 28. The shuttle body 144 may also include a protrusion 158 extending above the body 144 that may be used to align the shuttle assembly 110 within a handle track (not shown) at the top of the handle 26 and may partially protrude out of the handle 26 to indicate the position of the shuttle assembly 110 within the enclosed handle 26.

Figure 8:
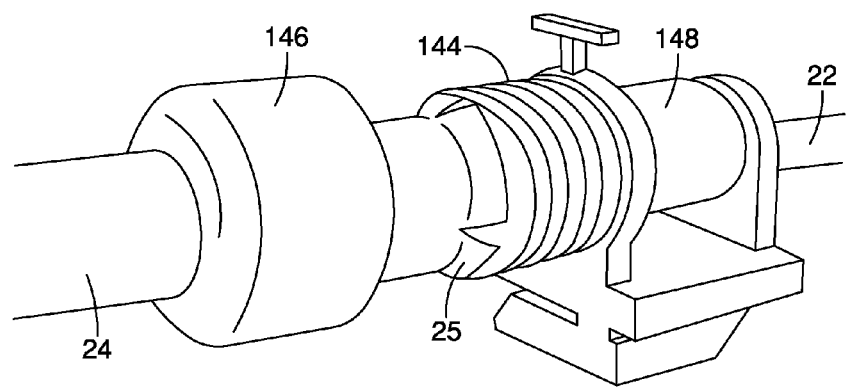
FIG. 8 illustrates the cap securing an outer sheath to the shuttle body of the flushing system.

A distal portion 160 of the shuttle body 144 may include a threaded portion 162 for connection with the cap 146. The cap 146 as shown in FIG. 6 includes an opening 164 connected to a lumen 168 extending through the cap 146. The opening 164 is sized and shaped to receive the outer sheath 24. The cap 146 may also include internal threads 170 to mate with the threads 162 of the shuttle body 144. The shuttle body 144 may also included a flared portion 163 for securing the outer sheath 24 between the shuttle body 144 and the cap 146. As shown in FIG. 8, the cap 146 may be positioned over a flared proximal end 25 of the outer sheath 24 to secure the outer sheath 24 between the cap 146 and the flared portion 163 of the shuttle body 144 of the shuttle assembly 110. FIG. 1 illustrates the cap 146 completely connected to the shuttle body 144 and the outer sheath 24 secured thereto. While the cap 146 and the distal end 160 of the shuttle body 144 are shown having corresponding threads 162, 170, the cap 146 may be connected to the distal portion 160 of the shuttle body 144 by any mechanism known by one skilled in the art including snap fit connections and the like.

The shuttle body 144 also includes a proximal portion 172 that is connectable to the check flow valve 148. The check flow valve 148 shown in FIG. 7 includes a first opening 174, a second opening 176 and a lumen 178 extending therebetween. The first opening 174 may include protrusions 180 that are configured to mate with protrusions 182 on the proximal portion 172 of the shuttle body 144 to form a leak proof connection. The check flow valve 148 may be connected to the proximal portion 172 of the shuttle body 144 using any type of connector that provides for a leak proof connection. As shown in FIG. 5C, a seal 173 such as an o-ring or tape may also be provided to facilitate the leak proof seal. The second opening 176 in the check valve 148 is sized and shaped to receive the inner catheter 22 therethrough. The check flow valve 148 is shown connected to the proximal portion 172 of the shuttle body in FIG. 8. The shuttle body 144 may also include an opening 175 that is configured to receive the tubing 114 as shown in FIG. 5C. The opening 175 connects to the lumen 152 to allow for flushing of the system 10 in all positions of the outer sheath 24.

Figure 9A:
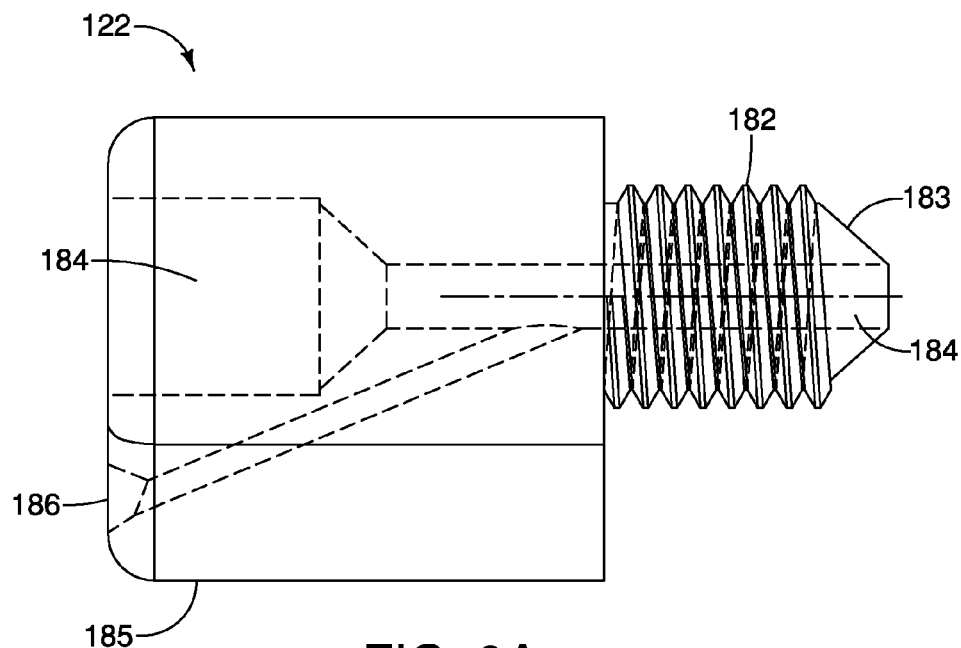
FIG. 9A is a side view of an embodiment of an end assembly of the flushing system.
Figure 9B:
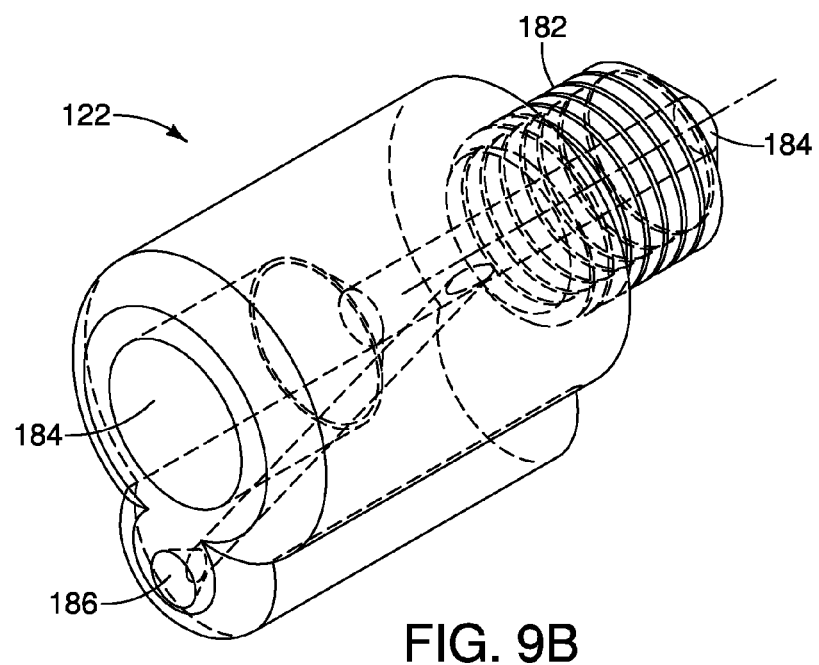
FIG. 9B is a perspective view of the end assembly shown in FIG. 9A.

An exemplary embodiment of the end assembly 122 is shown in FIGS. 9A and 9B. The end assembly 122 may be connected to the proximal end 30 of the handle 26 as shown in FIGS. 1 and 3. By way of non-limiting example, the end assembly 122 may include a threaded connection portion 182 at a distal end 183 of the end assembly 122. The end assembly 122 may be connected to the handle 26 by any means known to one skilled in the art and may be protruding from the handle 26. The end assembly 122 further includes a lumen 184 extending therethrough. The lumen 184 may be connected to the luer adaptor 124 at a proximal end 185 of the end assembly 122. The inner catheter 22 may extend through the lumen 184 and connect to the luer adaptor 124. A lumen (not shown) through the inner catheter 22 extends to the proximal end 30 of the handle 26 that is configured to receive a wire guide (not shown) therethrough. An additional lumen 186 may be provided in the end assembly 122 for reception of the lock wire 29 therethrough. The lumen 186 may connect to the lumen 184 in the end assembly 122 so that the lock wire 29 may extend through the inner catheter 22 to the end assembly 122 to avoid interference of the lock wire 29 with the fluid flow through the system 100.

Figure 10:
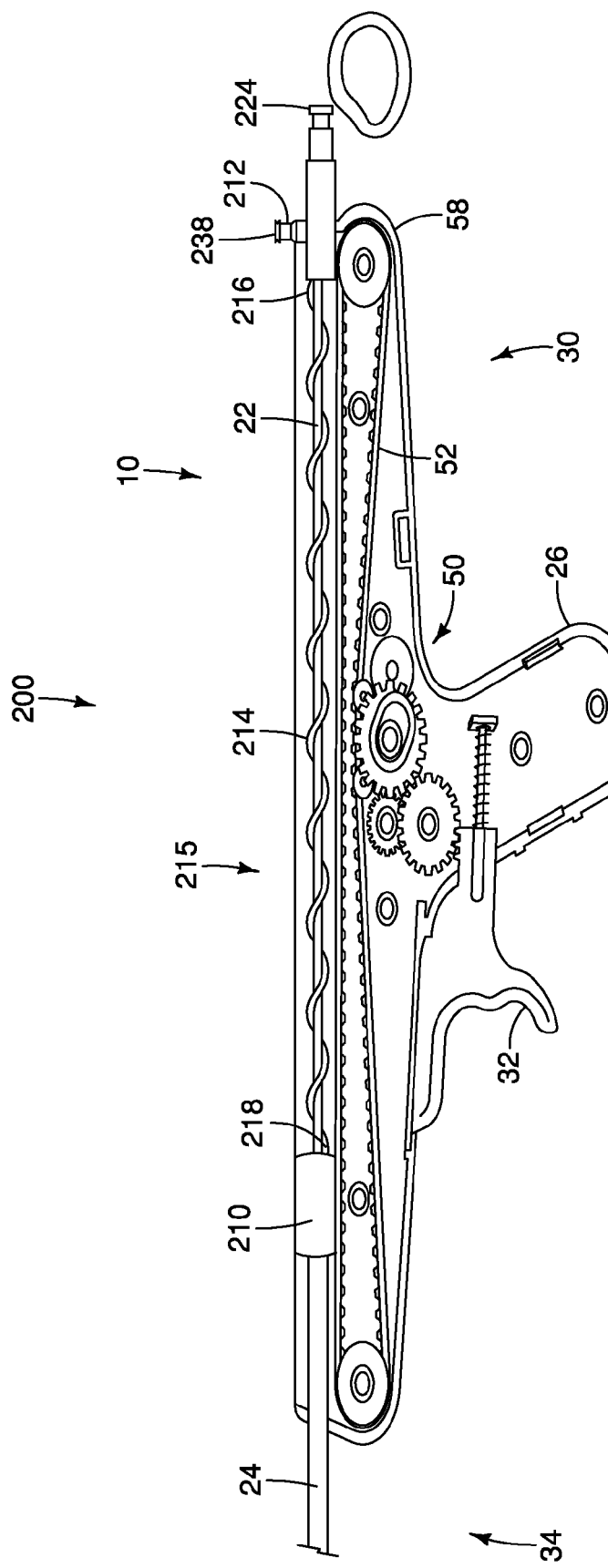
FIG. 10 is a partial side view of delivery system including an extendable flushing system having a proximal flush port.

An alternative embodiment of an extendable flushing system 200 is shown in FIG. 10. Similar to the extendable flushing system 100 described above, the extendable flushing system 200 is provided with a delivery device 10 including the inner catheter 22 and the outer sheath 24 that is coaxially movable relative to the inner catheter 22. The delivery system 10 includes the handle 26 at the proximal end 30 of the system 10 through which the inner catheter 22 and outer sheath 24 at least partially extend. The internal gear-pulley mechanism 50 allows bidirectional movement of the outer sheath 24. The movable belt 52 is connected to the internal gear-pulley mechanism 50 and to a shuttle assembly 210 that is operably connected to the outer sheath 24. Together the movable belt 52, the gear-pulley mechanism 50 and the shuttle 210 cooperate to longitudinally move the outer sheath 24 to expose and re-cover the stent 28 (shown in FIG. 2). The delivery system operates as explained above with reference to FIG. 1.

The extendable flushing system 200 shown in FIG. 10 is operably connected to the delivery system 10 that moves the outer sheath 24 relative to the inner catheter 22 in a controlled and accurate movement. The extendable flushing system 200 allows the physician to flush the delivery system 10 in all positions of the movable outer sheath 24. The extendable flushing system 200 includes the shuttle assembly 210, a proximal flush port 212 and a flexible tubing 214. As shown in FIG. 10, the extendable flushing system 200 has an extended configuration 215 where the shuttle assembly 210 is moved away from the proximal flush port 212 and towards the distal end 34 of the handle 26. The flexible tubing 214 is extended between the proximal flush port 212 and the shuttle assembly 210. As shown in FIG. 10, the proximal flush port 212 may be mounted on a proximal portion 58 of the handle 26 so that the proximal flush port 212 is in a fixed position relative to the handle 26. The shuttle assembly 210 is longitudinally movable within the handle 26 along the inner catheter 22 to move the outer sheath 24 proximally and distally relative to the inner catheter 22. The tubing 214 is connected to the proximal flush port 212 at a first end 216 of the tubing 214 and to the shuttle assembly 210 at a second end 218 of the tubing 214. The tubing 214 is similar to the tubing 114 described above and elongates and compresses as the shuttle assembly 210 moves proximally and distally. With the shuttle assembly 210 positioned near the distal end 34 of the handle 26 as shown in FIG. 10, the outer sheath 24 is extend over the stent 28. The tubing 214 of the extendable flushing system 200 may also be moved to a compressed configuration by moving the shuttle assembly 210 proximally toward the proximal port 212. See FIG. 3 illustrating a compressed configuration 117 for the tubing.

Figure 11:
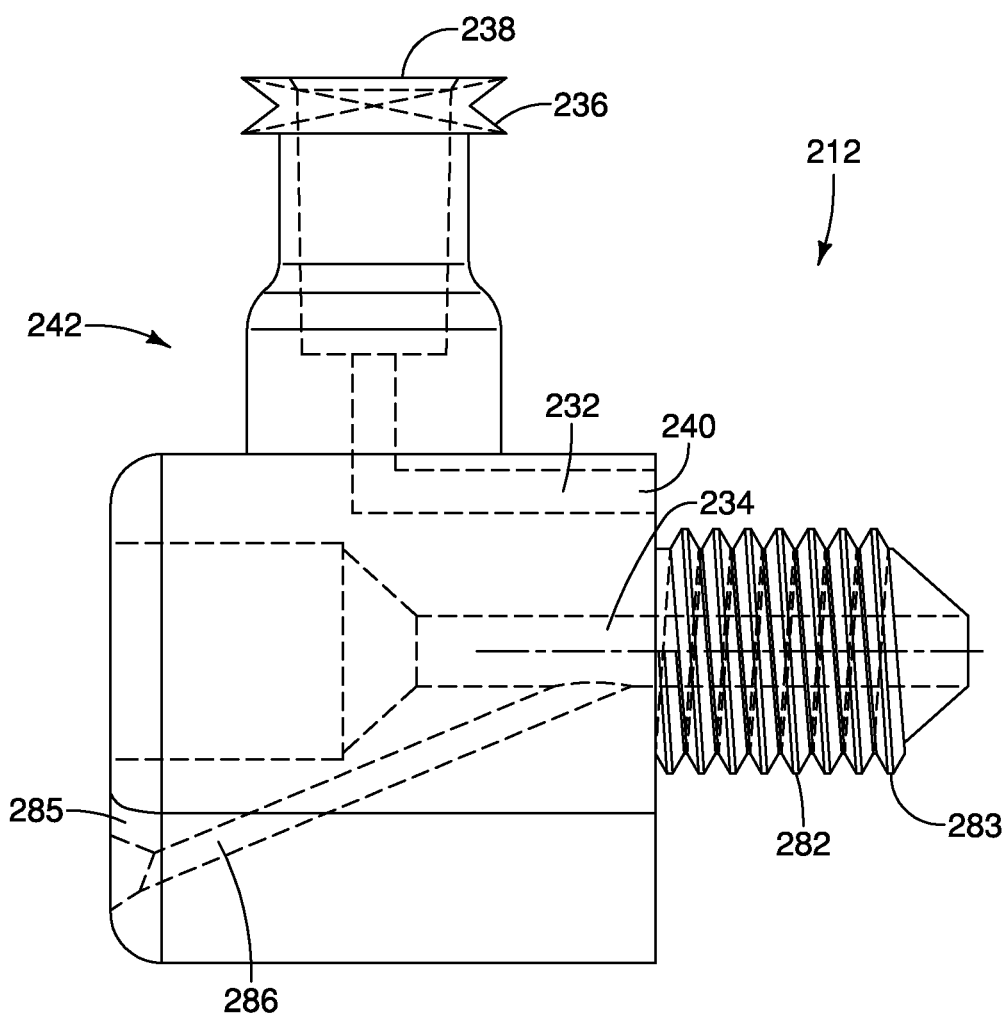
FIG. 11 is a side view of a proximal flush port of the flushing system.

An enlarged view of an exemplary proximal flush port 212 is shown in FIG. 11. The proximal flush port 212 includes a first lumen 232 and a second lumen 234. The first lumen 232 is configured to receive a fluid therethrough and the second lumen 234 is configured to receive the inner catheter 22. As shown, the proximal flush port 212 may include an adapter 236, such as a luer adapter, at a first opening 238 of the first lumen 232 for connection to a syringe or tubing to deliver the fluid through the first lumen 232. The first opening 238 may be provided on a top side 242 of the proximal flush port 212 to provide access to the flush port 212 during stent delivery. A second opening 240 of the first lumen 232 connects to the first end 216 of the tubing 214 to conduct the fluid through the tubing 214. (See FIG. 10.) The second lumen 234 is sized and shaped to allow the inner catheter 22 to be received therein. The inner catheter 22 may be slidably received through the second lumen 234 in embodiments having a movable inner catheter 22. In other embodiments, having the inner catheter 22 fixed in position relative to the outer sheath 24, the inner catheter 22 is fixed in position in the second lumen 234.

As shown in FIG. 11, the proximal flush port 212 may further include a threaded connection portion 282 at a distal end 283 of the proximal flush port 212 to connect the proximal port 212 to the handle 26. The proximal flush port 212 may be connected to the handle 26 by any means known to one skilled in the art. The second lumen 234 may be connected to a luer adaptor 224, shown in FIG. 10, at a proximal end 285. A lumen (not shown) through the inner catheter 22 extends to the proximal end 30 of the handle 26 that is configured to receive a wire guide (not shown) therethrough. An additional lumen 286 may be provided in the proximal flush port 212 for reception of the lock wire 29 therethrough. The lumen 286 may connect to the second lumen 234 in the proximal port 212 so that the lock wire 29 may extend through the inner catheter 22 out of the proximal end 30 of the handle 26 to avoid interference of the lock wire 29 with the fluid flow through the system 200.

The extendable flushing system 200 includes the shuttle assembly 210 that may be similarly configured to the shuttle assembly 110 as described above and shown in FIGS. 5A-7. The second end 218 of the flexible tubing 214 connects to the shuttle assembly 210 to provide a fluid connection between the proximal flush port 212 and the shuttle assembly 210 so that the lumen of the outer sheath 24 may be flushed at all positions of the outer sheath 24 relative to the inner catheter 22 as described above with reference to the system 100.

Figure 12:
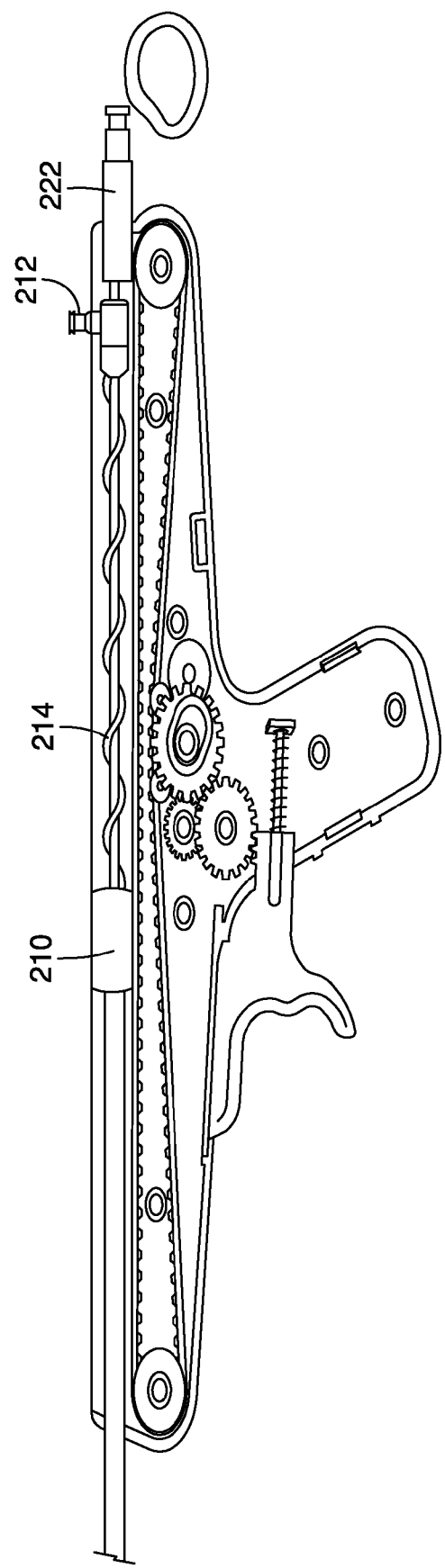
FIG. 12 is a partial side view of delivery system including an extendable flushing system having a proximal flush port.

The delivery system 200 may also be provided with the proximal flush port 212 and an end assembly 222 separate from the proximal flush port 212 as shown in FIG. 12. The proximal flush port 212 may be fixed in position or movable longitudinally within the handle 26. The shuttle assembly 210, the tubing 214 and the end assembly 222 may be configured similarly to the embodiments described above.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. An extendable flushing system for use with a medical device having an elongate shaft with a lumen extending therethrough, the extendable flushing system comprising:
    flexible tubing having an extended configuration and a compressed configuration, a first tubing end and a second tubing end;
    a flush port having a first lumen operably connected to the first tubing end and an opening configured to receive fluid therethrough;
    a shuttle assembly operably connected to the second tubing end forming a fluid flow path with the flush port and the shuttle assembly, the shuttle assembly configured to be fluidly connected to an elongate shaft lumen and the shuttle assembly movably positionable relative to the flush port and configured to move the flexible tubing between the compressed configuration and the extended configuration;
    an outer sheath operably connected to the flush port and the shuttle assembly and movably positionable with the shuttle assembly; and
    an inner catheter coaxially extendable through a lumen of the outer sheath, the shuttle assembly and the outer sheath longitudinally movable relative to the inner catheter.

2. The extendable flushing system of claim 1, wherein the shuttle assembly further comprises a cap and a shuttle body.

3. The extendable flushing system of claim 2, wherein a proximal end portion of the outer sheath is positioned between the cap and the shuttle body to retain the outer sheath on the shuttle assembly.

4. The extendable flushing system of claim 1, wherein the shuttle assembly further comprises a check flow valve.

5. The extendable flushing system of claim 1, wherein the flexible tubing comprises a coil.

6. The extendable flushing system of claim 1, wherein the flush port comprises a second lumen and the outer sheath is extendable therethrough.

7. The extendable flushing system of claim 1, wherein the flush port comprises a second lumen and the inner catheter is extendable therethrough.

8. The extendable flushing system of claim 1, wherein the inner catheter extends proximal to the shuttle assembly.

9. The extendable flushing system of claim 8, further comprising an end assembly operably connected to the inner catheter.

10. The extendable flushing system of claim 9, wherein the end assembly comprises a lumen configured to receive a lock wire therethrough.

11. The extendable flushing system of claim 1, further comprising a belt operably connected to the shuttle assembly to move the shuttle assembly and the outer sheath proximally and distally and to move the flexible tubing between the extended and compressed configurations.

12. A delivery system comprising:
   a handle having a proximal portion and a distal portion;
   an outer sheath comprising a lumen, the outer sheath at least partially positioned within the handle;
   an inner catheter coaxially positioned within at least a portion of the outer sheath, the outer sheath longitudinally movable relative to the inner catheter; and
   an extendable flushing system positioned at least partially within the handle, the extendable flushing system comprising:
      a flush port positioned at least partially within the handle, the flush port comprising a first lumen having an opening configured to receive fluid therethrough;
      flexible tubing having an extended configuration and a compressed configuration, a first tubing end and a second tubing end, the first tubing end operably connected to the first lumen; and
      a shuttle assembly positioned at least partially within the handle and operably connected to the second tubing end forming a fluid flow path with the flush port and the shuttle assembly, the shuttle assembly configured to be fluidly connected with the lumen of the outer sheath, the shuttle assembly movably positionable relative to the flush port and configured to move the flexible tubing between the compressed configuration and the extended configuration.

13. The delivery system of claim 12, wherein the flush port is positioned distal to the shuttle assembly.

14. The delivery system of claim 12, wherein the flush port is positioned proximal to the shuttle assembly.

15. The delivery system of claim 12, wherein the inner catheter is fixed in position relative to the handle.

16. The delivery system of claim 12, further comprising a stent positioned about the inner catheter.

17. A method of flushing a delivery system having an outer sheath movable relative to an inner catheter, the method comprising:
   providing an extendable flushing system comprising:
      flexible tubing having an extended configuration and a compressed configuration, a first tubing end and a second tubing end;
      a flush port having a first lumen operably connected to the first tubing end and an opening configured to receive fluid therethrough;
      a shuttle assembly operably connected to the second tubing end forming a fluid flow path with the flush port and the shuttle assembly, the shuttle assembly movably positionable relative to the flush port and configured to move the flexible tubing between the compressed configuration and the extended configuration;
      an outer sheath operably connected to the flush port and the shuttle assembly and movably positionable with the shuttle assembly; and
      an inner catheter coaxially extendable through a lumen of the outer sheath, the shuttle assembly and the outer sheath longitudinally movable relative to the inner catheter;
   connecting a fluid source to the opening in the flush port; and
   injecting fluid into the port, through the tubing to the shuttle assembly and into a lumen of the outer sheath.

* * * * *